(12) United States Patent
Wilborn et al.

(10) Patent No.: US 9,950,143 B2
(45) Date of Patent: Apr. 24, 2018

(54) INTRAVENOUS SPLINT COVER AND ASSOCIATED METHODS

(71) Applicant: Marie-Andrea I. Wilborn, Melbourne, FL (US)

(72) Inventors: Marie-Andrea I. Wilborn, Melbourne, FL (US); Marie Therese R. Fongemie, Melbourne, FL (US)

(73) Assignee: Marie Andrea I. Wilborn, Melbourne, FL (US)

( * ) Notice: Subject to any disclaimer, the term of this patent is extended or adjusted under 35 U.S.C. 154(b) by 338 days.

(21) Appl. No.: 14/699,766

(22) Filed: Apr. 29, 2015

(65) Prior Publication Data
US 2016/0317785 A1    Nov. 3, 2016
US 2017/0136214 A9    May 18, 2017

Related U.S. Application Data

(63) Continuation-in-part of application No. 13/367,498, filed on Feb. 7, 2012.

(51) Int. Cl.
*A61M 25/02*      (2006.01)
*A61F 13/10*      (2006.01)
(Continued)

(52) U.S. Cl.
CPC ............ *A61M 25/02* (2013.01); *A61F 5/058* (2013.01); *A61F 13/101* (2013.01); *A61F 2013/00272* (2013.01)

(58) Field of Classification Search
CPC ... A61M 25/02; A61F 15/008; A61F 13/0273; A61F 13/101; A61F 5/058
See application file for complete search history.

(56) References Cited

U.S. PATENT DOCUMENTS 2,280,506 A    4/1942   Betts
2,734,503 A    2/1956   Doyle
(Continued)

FOREIGN PATENT DOCUMENTS

WO    WO 2011/040815 A1    4/2011
WO    WO 2013/018055 A2    4/2013

OTHER PUBLICATIONS

USPTO's Office Action dated Apr. 13, 2013 in related by reference U.S. Appl. No. 13/367,498, filed Aug. 16, 2013 (10 pages).

(Continued)

*Primary Examiner* — Bradley Osinski
(74) *Attorney, Agent, or Firm* — Mark Malek; Widerman Malek, PL

(57) ABSTRACT

An intravenous splint cover may include a main body, a pair of opposing securing members, and a splinting member. The main body may be rectangular shaped and have a bottom portion and a top portion. The pair of opposing securing members may be rectangular shaped and be connected to and extend outwardly from the main body and have a bottom portion and a top portion. The splinting member may be rectangular shaped and be carried by the bottom portion of the main body and extend outwardly from the main body to create an elevated portion of the main body. The bottom portions of the pair of opposing securing members may have an adhesive material applied thereto. The bottom portion of the main body that does not carry the splinting member may have an adhesive material applied thereto.

23 Claims, 8 Drawing Sheets

(51) Int. Cl.
*A61F 5/058* (2006.01)
*A61F 13/00* (2006.01)

(56) References Cited

U.S. PATENT DOCUMENTS

| | | | |
|---|---|---|---|
| 2,992,644 A | 7/1961 | Plantinga et al. |
| 3,156,242 A | 11/1964 | Crowe |
| 3,196,870 A | 7/1965 | Sprecher et al. |
| 3,490,448 A | 1/1970 | Grubb |
| 3,520,306 A | 7/1970 | Gardner et al. |
| 3,776,225 A | 12/1973 | Lonardo |
| 4,245,630 A * | 1/1981 | Lloyd ................ A61F 13/0203 428/167 |
| 4,425,913 A | 1/1984 | Lewis |
| 4,449,975 A | 5/1984 | Perry |
| 4,453,933 A | 6/1984 | Speaker |
| 4,457,754 A | 7/1984 | Buttaravoli |
| 4,557,723 A | 12/1985 | Sibalis |
| 4,619,253 A | 10/1986 | Anhauser et al. |
| 4,862,904 A | 9/1989 | West et al. |
| 5,000,741 A | 3/1991 | Kalt |
| 5,037,397 A | 8/1991 | Kalt et al. |
| 5,084,026 A | 1/1992 | Shapiro |
| 5,116,324 A | 5/1992 | Brierley et al. |
| 5,131,412 A | 7/1992 | Rankin |
| 5,160,328 A | 11/1992 | Cartmell et al. |
| 5,266,401 A | 11/1993 | Tollini |
| 5,304,146 A | 4/1994 | Johnson et al. |
| 5,380,294 A | 1/1995 | Persson |
| 5,413,562 A | 5/1995 | Swauger |
| 5,423,737 A | 6/1995 | Cartmell et al. |
| 5,437,619 A | 8/1995 | Malewicz et al. |
| 5,538,500 A | 7/1996 | Peterson |
| 5,690,610 A * | 11/1997 | Ito ................ A61F 13/0203 602/46 |
| 5,702,371 A | 12/1997 | Bierman |
| 5,807,295 A * | 9/1998 | Hutcheon ................ A61F 5/01 602/42 |
| 5,843,025 A | 12/1998 | Shaari |
| 5,891,074 A | 4/1999 | Cesarczyk |
| D409,754 S | 5/1999 | Dunshee et al. |
| 6,113,577 A | 9/2000 | Hakky et al. |
| 6,124,520 A | 9/2000 | Roberts |
| 6,258,066 B1 | 7/2001 | Urich |
| 6,375,639 B1 | 4/2002 | Duplessie et al. |
| 6,447,485 B2 | 9/2002 | Bierman |
| 6,526,981 B1 | 3/2003 | Rozier et al. |
| 6,663,600 B2 | 12/2003 | Bierman et al. |
| 6,809,230 B2 | 10/2004 | Hancock et al. |
| 6,827,707 B2 | 12/2004 | Wright et al. |
| 7,012,170 B1 | 3/2006 | Tomaioulo |
| 7,022,111 B2 | 4/2006 | Duplessie et al. |
| 7,182,088 B2 | 2/2007 | Jenkins |
| 7,294,752 B1 | 11/2007 | Propp |
| 7,723,561 B2 | 5/2010 | Propp |
| 7,799,001 B2 | 9/2010 | Bierman |
| 8,006,699 B2 | 8/2011 | Rozier et al. |
| 8,211,063 B2 | 7/2012 | Bierman et al. |
| 8,394,067 B2 | 3/2013 | Bracken et al. |
| 8,450,553 B2 | 5/2013 | Utterberg et al. |
| 2003/0055382 A1 | 3/2003 | Schaeffer |
| 2004/0220505 A1 | 11/2004 | Worthley |
| 2005/0256438 A1 | 11/2005 | Lobardozzi |
| 2007/0156070 A1 | 7/2007 | Schwab |
| 2008/0200880 A1 | 8/2008 | Kyvik et al. |
| 2008/0256438 A1 | 10/2008 | Harman et al. |
| 2009/0234296 A1 | 9/2009 | Robison |
| 2009/0254040 A1 | 10/2009 | Bierman et al. |
| 2011/0054409 A1 | 3/2011 | Nishtala |
| 2011/0224593 A1 | 9/2011 | Tunius |
| 2011/0288486 A1 | 11/2011 | Rozier et al. |
| 2011/0295174 A1 | 12/2011 | Richards |
| 2012/0277648 A1 | 11/2012 | Kendall |
| 2013/0012883 A1 | 1/2013 | Fitzgeral et al. |

OTHER PUBLICATIONS

USPTO's Final Office Action dated Jun. 26, 2013 in related by reference U.S. Appl. No. 13/367,498, filed Aug. 16, 2013 (14 pages).

USPTO's Adivsory Action dated Sep. 24, 2013 in related by reference U.S. Appl. No. 13/367,498, filed Aug. 16, 2013 (4 pages).

USPTO's Office Action dated Dec. 17, 2013 in related by reference U.S. Appl. No. 13/367,498, filed Aug. 16, 2013 (16 pages).

USPTO's Final Office Action dated Apr. 16, 2014 in related by reference U.S. Appl. No. 13/367,498, filed Aug. 16, 2013 (19 pages).

USPTO's Advisory Action dated Aug. 8, 2014 in related by reference U.S. Appl. No. 13/367,498, filed Aug. 16, 2013 (4 pages).

USPTO's Office Action dated Mar. 26, 2015 in related by reference U.S. Appl. No. 13/367,498, filed Aug. 16, 2013 (17 pages).

USPTO's Final Office Action dated Jul. 17, 2015 in related by reference U.S. Appl. No. 13/367,498, filed Aug. 16, 2013 (20 pages).

USPTO's Interview Summary dated Nov. 6, 2015 in related by reference U.S. Appl. No. 13/367,498, filed Aug. 16, 2013 (15 pages).

* cited by examiner

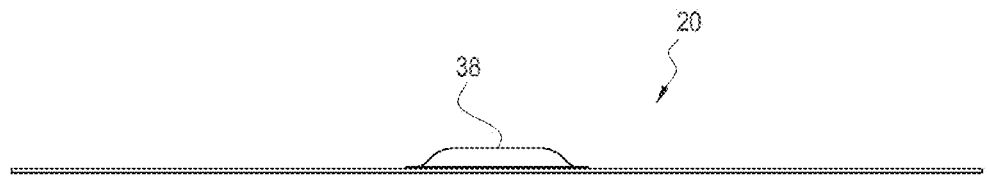
Fig. 5
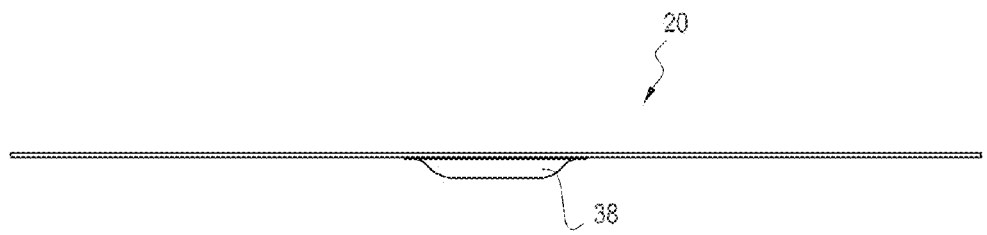
Fig. 6
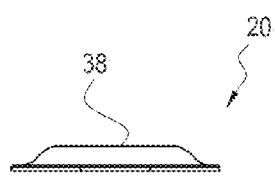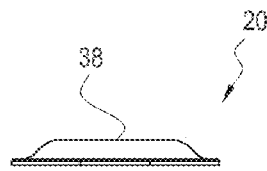
Fig. 7　　　Fig. 8

INTRAVENOUS SPLINT COVER AND ASSOCIATED METHODS

RELATED APPLICATIONS

This application is a continuation-in-part and claims the benefit under 35 U.S.C. § 120 of U.S. patent application Ser. No. 13/367,498 filed on Feb. 7, 2012 and titled Intravenous Splint Cover and Associated Methods, the entire contents of which are incorporated herein by reference herein in its entirety except to the extent disclosure therein is inconsistent with disclosure herein.

FIELD OF THE INVENTION

The present invention relates to the medical field and, more specifically, to the field of intravenous splint covers and associated methods.

BACKGROUND OF THE INVENTION

It can sometimes be uncomfortable when patients require medical treatment that involves an intravenous line (IV). Although IV medical treatment is very common, and is a routine way to deliver medication, the starting of an IV is generally a process that many patients do not like, i.e., being stuck with a needle. In some instances, an IV may come out, i.e., require reinsertion, thereby causing discomfort to the patient, and exposing the patient to possible infection. Another issue that may arise is occlusion of the IV due to the bending of an IV tube.

There have been attempts to prevent an IV from coming out such as, for example, immobilizing the patient's extremity where the IV is positioned. U.S. Pat. No. 4,425,913 to Lewis discloses a splint for supporting the hand, wrist and forearm of a patient when the patient is connected to an IV. The splint incorporates a substantially rigid molded body. Accordingly, use of the splint disclosed in the Lewis' 913 patent immobilizing a patient's extremity and can be uncomfortable for the patient. U.S. Pat. No. 3,776,225 to Lonardo also discloses a splint for supporting and maintaining a patient's forearm immobile while receiving an IV injection. Similar to the Lewis '913 patent, the Lonardo '225 patent is directed to immobilizing the patient's extremity and suffers from the same deficiency. Further, in cases where a patient may have edema, such devices do not stretch, which may cause fluid collection and clotting, which can, in turn, be problematic.

U.S. Pat. No. 7,182,088 to Jenkins discloses yet another arm immobilizer to be used when a patient is receiving IV treatments. The immobilizer described in the Jenkins '088 patent includes a closable sleeve of a compressible material which can be placed around the patient's arm above and below the elbow joint with an opening on the inside of the arm position to give access to the IV site. Although the device described in the Jenkins '088 patent provides for smaller movements of the patient's arm, it is still designed to prevent excesses flexure movement of the elbow. Further, this device uses metal and plastic materials in its construction. Accordingly, such device can be uncomfortable for the patient to wear on receiving IV treatments. This device can also impede circulation by constriction and limited extremity movement.

U.S. Pat. No. 7,799,001 to Bierman discloses a catheter securement device that holds a medical article upon the body of the patient and inhibits longitudinal movement of the medical article as can be seen in the figure below. The device disclosed in the Bierman '001 patent includes a central channel into which a portion of the IV may be inserted. Such a device may, however, be uncomfortable for patient, and may still inhibit flexural movement of the patient's extremity. This device's only purpose is to prevent dislodging of the catheter, needle, etc. and does not prevent bending or kinking of the catheter, needle, etc. Further, the device illustrated in the Bierman '001 patent may be expensive to manufacture.

U.S. Pat. No. 3,196,870 to Sprecher et al. discloses a limb immobilizer for intravenous feeding. This immobilizer may be used to cause the limb of the patient to remain straight and immobile while receiving IV treatments. More particularly, the illustrated version of the Sprecher et al. '870 patent is directed to immobilizing the upper and lower arms of a human to prevent movement of the elbow joint, thereby facilitating intravenous administration of food, blood or other fluids. This device is made of uncomfortable materials, such as metals and plastics. Such a system depicts the very problem that needs to be addressed, i.e., immobilization of the extremities of the patient, thereby causing discomfort.

U.S. Pat. No. 7,294,752 to Propp discloses a window-dressing with an integral anchor that includes a fabric layer having an insertion site viewing member. More specifically, and as perhaps best illustrated in FIG. 4 of Propp, the dressing includes a window through which the intravenous site may be readily viewed at all times while the device is in use. The Propp dressing is positioned over an insertion point of an intravenous site so that the catheter remains visible to both the medical professional and the patient. The remainder of the catheter, needle, etc. is positioned over the splinting member of the device. Such a device allows patients to view the insertion point at all times, even when a patient would desire not to view the insertion point. This can be an issue with patients that may suffer from dementia who may attempt to rip out an IV, or young patients that may be anxious from the sight of the IV. In addition, such a device may still inhibit flexural movement of the patient's extremity. This device is a clear dressing with an anchor to prevent dislodging of the catheter, needle, etc. and does not prevent bending or kinking of the catheter, needle, etc. Further, the device may be expensive to manufacture.

U.S. Pat. No. 5,702,371 to Bierman discloses a side loaded securement device using an anchoring device to securely anchor a catheter and fluid supply to a patient's skin as illustrated in FIG. 1 thereof. Such a device may, however, be uncomfortable for the patient, and may still inhibit flexural movement of the patient's extremity. Further, the device may be expensive to manufacture and may require specific tubing, catheters, needles, etc. so that they can matingly engage the device. Another disadvantage of the Bierman device is that it still allows for a patient to readily view the IV site, which causes the same issues referenced above with respect to the Propp reference. This device is used to prevent dislodging of the catheter, needle, etc. and does not prevent bending or kinking of the catheter, needle, etc.

U.S. patent application Ser. No. 12/027,963 by Chong discloses a particular adhesive material applied to the bottom portions of the securing members having stronger adhesive properties than the adhesive material that is applied to the main body as illustrated in FIG. 9 thereof. The device in Chong, however, discloses applying a stronger adhesive to different areas of the base of a medical device, but not to the securing members when they are separate from the main body. In addition, Chong is not an intravenous splint cover and does not allow any flexural movement of a patient's extremity when a catheter, needle, etc. is in place.

U.S. Pat. No. 5,084,026 to Shapiro discloses an anchor pad with straps for securing the pad to an extremity of a patient. Two latch arrangements for holding the tubing and needle section of an intravenous apparatus are attached to the top face of the pad. Shapiro suffers from the same defects as the '371 Bierman reference. This device is an anchor and does not protect the catheter, needle, etc. or the IV site.

U.S. Pat. No. 3,490,448 to Grubb discloses a surgical bandage with an adhesive backing, a thick, sterile pressure pad, and a pair of removable protective strips as illustrated in FIGS. 9 and 10 thereof. The device is specifically used when a needle is removed from the skin of a patient. The device described in Grubb is used to apply pressure over the puncture to minimize bleeding. The device disclosed in Grubb cannot be used over an intravenous site as it will prevent the flow of fluid through the IV line and into the patient. In other words, the device described in Grubb is a pressure device that is used to prevent the flow of fluid (for example blood) at the IV site, i.e., where the puncture is made using the needle. Grubb only describes the thick, sterile pressure pad attached to the backing forming a wound contacting area. The device is a pressure bandage only used after a catheter, needle, etc. has been removed.

U.S. Pat. No. 5,891,074 to Cesarczyk discloses a device that puts pressure on the intravenous wound site, thus acting as a pressure wound dressing as illustrated in FIGS. 7 and 8 thereof. The pressure exerting support member of the device is designed with two substantially planar surfaces with the second surface extending from the first surface at an angle away from the flexible support layer at an acute angle. The pliant absorbent material layer is placed against the wound site, not over the entire intravenous site. Once the needle is removed, the device is attached firmly to the patient over the wound site. Cesarczyk suffers from the same defects as the '448 Grubb reference in that it is inappropriate for use in connection with the delivery of fluid through an IV. Instead, the device described in the Cesarczyk is adapted to be used after an IV has been removed so that the wound created by the IV on the patient's skin may be readily healed. This device, along with the device described in the Grubb reference, are inappropriate for simultaneous use with an IV and/or IV therapy.

As can be seen in FIG. 17, when an IV and IV tube are in a working position, the IV and IV tube are not bent or kinked so as to allow the ready flow of fluids.

When a patient bends his/her arm, however, or any adjacent extremity to an IV site, shifting, kinking or bending of a flexible catheter, needle, cannula, flexible tube, etc. in the vein located in a bend of the patient's extremity is not addressed by any of these devices. Compression of the catheter, needle, cannula, flexible tube, etc. against the vessel wall is also a problem with these devices. As can be seen in FIG. 18, pivoting of a joint or bony area causing bending and kinking of the catheter, needle, cannula, flexible tube, etc. or a positional IV often causes compression of a flexible catheter, needle, cannula, flexible tube, etc. against a bony prominence restricting IV therapy, i.e., transfer of a substance, such as a fluid, into a patient.

In addition, in the prior art, the IV site is either covered so that it is not accessible and/or viewable, without the ability to view or palpate, covered with a transparent material, or not addressed by the prior art device. No flexibility exists in these viewing conditions. There is no device that covers the IV site, thus preventing accidental viewing of the IV site, except when desired, such as when a medical professional needs to view the IV site. Instead, the patient can either always view the IV site or the device must be removed to allow a person to view the IV site, thus requiring another device to be used. Accordingly, a need exists for an intravenous splint cover that does not restrict movement of the patient and that allows the patient to engage in activities of daily living. There also exists a need for an intravenous splint cover that simultaneously secures an IV site so as to prevent any need for reinsertion of an IV. Finally, a need exists for an intravenous splint cover that covers and protects the IV site, remains in place yet allows a medical professional or other person to view the IV site when desired without damaging the device or requiring the device's removal.

The devices described above, and other devices that may be known in the art generally suffer from the same deficiency, i.e., the devices prevent the patient from being able to move their extremity. Such restriction on movement also interferes with activities of daily living of the patient and immobilizes an area decreasing circulation and/or impeding blood flow. Patients that are uncomfortable while receiving IV treatments may not respond as well to treatment as patients who are comfortable.

SUMMARY OF THE INVENTION

The intravenous splint cover according to an embodiment of the present invention advantageously contours to the patient's extremity where the IV is located so that the patient may maintain mobility and flexibility of the extremity while receiving IV treatments. The intravenous splint cover according to an embodiment of the present invention also advantageously does not immobilize extremities or joints of the patient and promotes comfort of the patient while receiving IV treatments. The intravenous splint cover according to an embodiment of the present invention further advantageously conceals the IV site, thereby directing the patient's attention away from the IV site, and preventing the patient from removing the IV. The present invention still further advantageously allows the IV site to remain accessible, and decreases the risk of occlusions of the IV catheter, needle, cannula, flexible tube, etc. due to shifting, crimping and bending from flexion, bone rotation and movement. Decreasing the risk of occlusions on the IV catheter also advantageously decreases the instances of reinsertion of the IV, thereby decreasing the risk of infection. Decreasing crimping and bending of the IV catheter may also reduce the need to insert the IV catheter in other locations or other devices such as invasive midlines, peripheral inserted central catheters, or central vascular inserted catheter lines.

These and other features and advantages according to an embodiment of the present invention are provided by an intravenous (IV) splint cover that includes a main body having a bottom portion and a top portion. The IV splint cover may also include a pair of opposing securing members connected to and extending outwardly from the main body. Each of the pair of opposing securing members may have a bottom portion and a top portion. The IV splint cover may further include a splinting member carried by the bottom portion of the main body and extending outwardly from the main body to create an elevated portion of the main body.

The bottom portions of the pair of opposing securing members may have an adhesive material applied thereto, and the bottom portion of the main body that does not carry the splinting member may also have an adhesive material applied thereto. The splinting member may be non-adhesive and may extend along the bottom portion of the main body substantially between an entire width thereof, and may be carried by a medial portion of the main body. Therefore, the IV splint cover according to an embodiment of the present invention may advantageously secure and protect an IV on the extremity of the patient while simultaneously providing mobility to the extremity of the patient where the IV is positioned and allowing for ready viewing of the IV by a medical professional, as necessary.

Each of the pair of opposing securing members may include a respective pair of spaced apart securing members. Each of the respective pair of spaced apart securing members may extend substantially parallel to one another. The splinting member may be raised along a medial portion of the main body and may taper downwardly towards side portions of the main body. The IV splint cover according to an embodiment of the present invention may further include an adhesive cover member to be removeably positioned over the main body, the securing members and the splinting member. The adhesive cover member may be provided by a pair of adhesive cover members. A first one of the pair of adhesive cover members may extend from an end portion of one of the securing members to a medial portion of the splinting member, and a second one of the pair of adhesive cover members extends from an end portion of a second one of the securing member to the medial portion of the splinting member.

The adhesive material that may be applied to the bottom portions of the securing members may have stronger adhesive properties than the adhesive material that may be applied to the main body. This advantageously provides the ability for the IV splint cover to be readily secured to the patient so as to provide enhanced adhesive properties to the securing members to, in turn, provide for enhanced ability of the IV splint cover to remain applied over the IV site. The main body and the pair of opposing securing members may be integrally formed as a monolithic unit. This advantageously enhances manufacturing efficiency of the IV splint cover and decreases the cost of manufacturing. The main body and the pair of opposing securing members may be provided by a substantially flexible material, a substantially stretchable material, a biodegradable material, a hypoallergenic material, a breathable material, a porous material, and/or a latex-free material.

A method aspect of the present invention is for using an IV splint cover. The method may include exposing the bottom portions of the main body, the pair of opposing securing members and the splinting member. The method may further include applying the splinting member to an IV site on a patient by centering the splinting member over the IV site. The method may still further include securing the splinting member to the IV site by affixing the securing members to an extremity of the patient. This is preferably performed so that the main body of the IV splint cover and the opposing securing member are applied to the extremity of the patient where the IV is positioned so as not to immobilize the extremity and so that the IV site is readily accessible and better protected.

BRIEF DESCRIPTION OF THE DRAWINGS

FIG. 5 is a right-side elevation view of the intravenous splint cover illustrated in FIG. 1.

FIG. 6 is a left-side elevation view of the intravenous splint cover illustrated in FIG. 1.

FIG. 7 is a front elevation view of the intravenous splint cover illustrated in FIG. 1.

FIG. 8 is a rear elevation view of the intravenous splint cover illustrated in FIG. 1.

DETAILED DESCRIPTION OF THE PREFERRED EMBODIMENT

Figure 1:
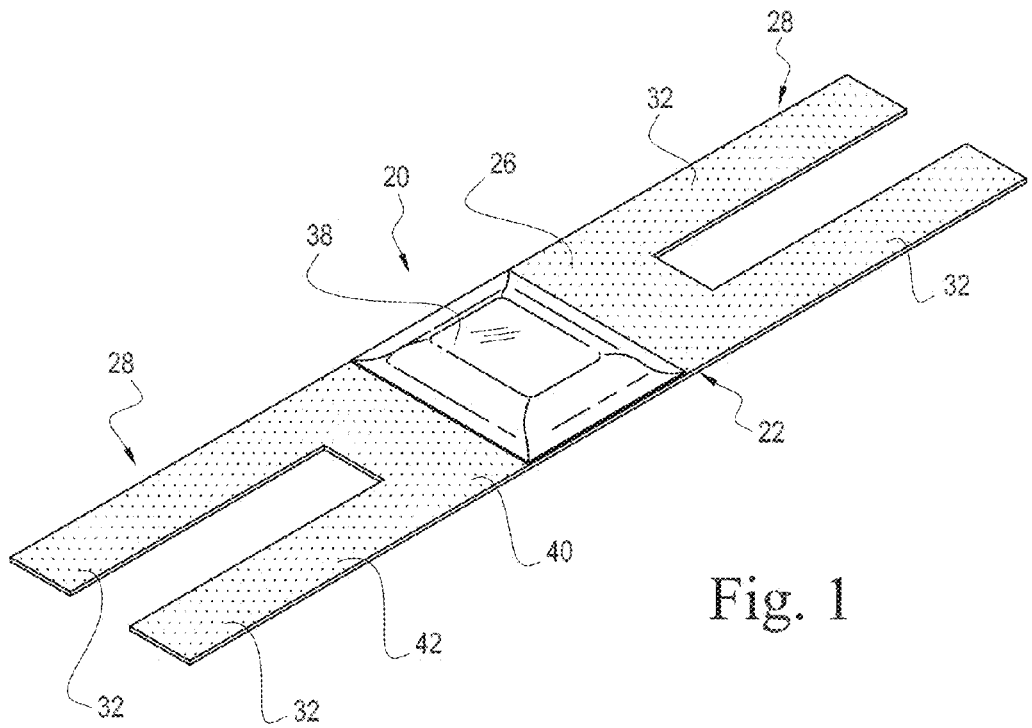
FIG. 1 is a bottom perspective view of an intravenous splint cover according to an embodiment of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notations, if used, refer to similar elements in alternate embodiments.

In this detailed description of the present invention, a person skilled in the art should note that directional terms, such as "above," "below," "upper," "lower," "medial," "center," and other like terms are used for the convenience of the reader in reference to the drawings and the accompanying descriptions. Also, a person skilled in the art should notice this description may contain other terminology to convey position, orientation, and direction without departing from the principles of the present invention. The terms pivot, bend, and rotate and other derivations of these words are often used interchangeably and should not be considered limiting in any way. The terms catheter, needle, cannula, flexible tube, IV, and other similar terms and other derivations of these words are often used interchangeably and should not be considered limiting in any way. Those skilled in the art will appreciate that many variations and alterations to the descriptions contained herein are within the scope of the invention.

Further, throughout this specification, the invention is referred to as an intravenous splint cover 20. Intravenous may sometimes be abbreviated as IV, and is not meant to be limiting in any way to the invention, as defined by the claims appended hereto. Throughout this disclosure, the intravenous splint cover 20 may be referred to as the IV splint cover, the splint cover, the system, the device, the apparatus or the invention. Alternate references to the intravenous splint cover 20 in this disclosure are not meant to be limiting in any way. Those skilled in the art will appreciate that an IV line 80, a line connected to a catheter 81, needle, cannula, flexible tube, etc. that is or has been inserted into a patient and is typically designed for IV therapy, may be positioned anywhere on a patient, including but not limited to any area and any body part, and, although the appended drawings illustrate an IV site 90 being positioned on an arm of a patient, the present invention advantageously may be used regardless of the positioning of the IV line 80 on the patient. The present invention is also not meant to be limited to use in connection with IV lines 80. Those skilled in the medical field will appreciate that the present invention can advantageously be used in connection with arterial lines and for dialysis lines, as well as other known treatments.

The IV site 90 includes the puncture area or wound area where the catheter 81, needle, cannula, flexible tube, etc. is inserted as well as the area of the skin over or above the inserted catheter 81, needle, cannula, flexible tube, etc. Once the catheter 81, needle, cannula, flexible tube, etc. is introduced into the vein (and often portions are removed, such as the needle from the catheter 81, cannula, flexible tube, etc.), the remaining portion remains in place for IV therapy. In the insertion process, the catheter 81, cannula, flexible tube, etc. may be over a needle or similar device. Once the needle or similar device and catheter 81, cannula, flexible tube, etc. are inserted into a vein or artery, the needle may be removed and the catheter 81, cannula, flexible tube, etc. may be left in place for IV therapy. An end hub of the catheter 81, cannula, flexible tube, etc. may then be connected to the IV line 80 which may have an extension with a port on the end that may be accessed for Intravenous fluid delivery. The IV site 90 may then be covered by a clear or transparent sterile dressing which may leave the extension and port accessible for clinicians to deliver fluids for IV therapy.

The IV splint cover 20 may cover the IV site 90 entirely and additionally cover other areas near the IV site 90. For example, and without limitation, in addition to the IV site 90, the IV splint cover 20 may cover a remaining portion of the catheter 81, needle, cannula, flexible tube, etc. that is not inserted in the patient. As another example, and without limitation, in addition to the IV site 90, the IV splint cover 20 may cover a portion of the IV line 80. The IV site 90 may also include areas of the patient's skin adjacent to the catheter 81, needle, cannula, flexible tube, etc. As yet another example, and without limitation, the IV site 90 may include a flexible tube catheter, sterile occlusive dressing to cover the insertion point extending from the length of the cannula to the extension set IV line 80, and an anchor or other stabilizing device. For example, and without limitation, the IV site 90 may include a flexible tube venous catheter in the vein covered by a sterile occlusive dressing to cover the insertion point extending from the length of the cannula to the extension set IV line 80 leaving the port on the end of the extension line accessible for fluid delivery and/or IV therapy.

The IV site 90 may also be described as comprising a catheter 81 or cannula which may also be called a flexible tube. A catheter hub may be connected to the IV line 80 which may also be called an extension tubing or a line. The IV site 90 may be covered by a clear or transparent sterile dressing. At the end of the IV line 80 the extension tubing may be a port for a clinician to access and deliver fluids to the patient for IV therapy.

Figure 2:
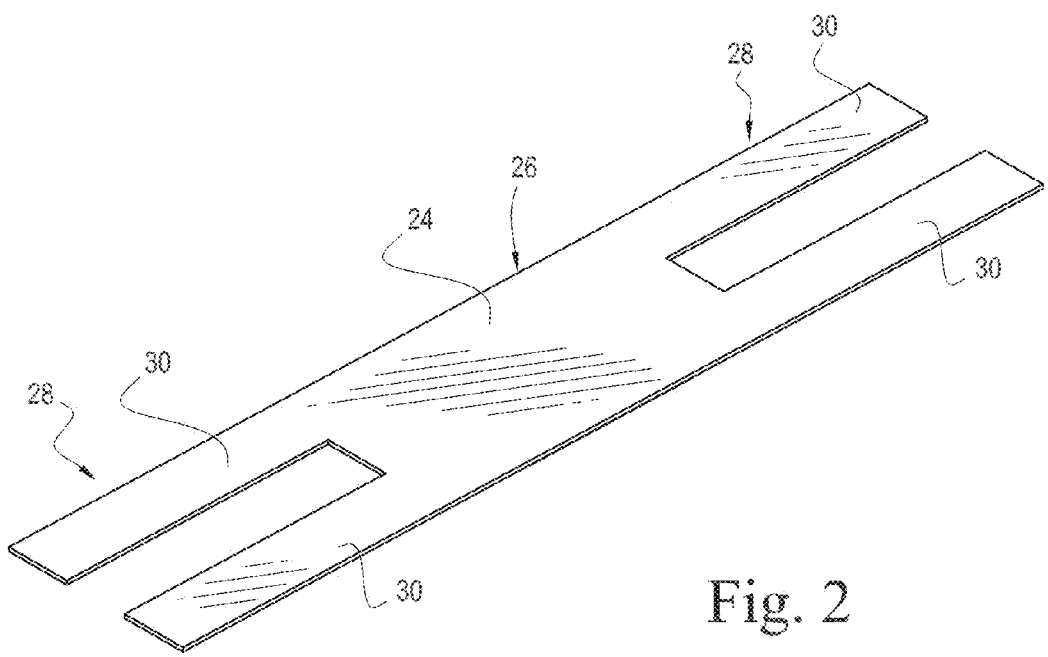
FIG. 2 is a top perspective view of the intravenous splint cover illustrated in FIG. 1.

Referring now to FIGS. 1 and 2, details of the intravenous splint cover 20 and methods according to an embodiment of the present invention are now discussed in greater detail. The intravenous splint cover 20 may include a main body 22. The main body 22 may be illustratively defined by a medial portion of the intravenous splint cover 20. As illustrated in FIGS. 1 and 2, the main body 22 of the intravenous splint cover 20 may include a bottom portion 26 and a top portion 24.

As further illustrated in FIGS. 1 and 2, the intravenous splint cover 20 may include a pair of opposing securing members 28 that are connected to and extend outwardly from the main body 22. Each of the pair of the opposing securing members 28 may also have a bottom portion 32 and a top portion 30. The intravenous splint cover 20 according to an embodiment of the present invention may also include a splinting member 38 that is carried by the bottom portion 26 of the main body 22. The splinting member 38 illustratively extends outwardly from the main body 22 of the intravenous splint cover 20 to create an elevated portion of the main body 22. More specifically, and with reference to FIG. 1, the splinting member 38 is also positioned along a medial portion of the main body 22 and, in the illustrated embodiment, along a medial portion of the IV splint cover 20. Those skilled in the art will appreciate, however, that the positioning of the splinting member 38 should not be limited to a medial portion of the IV splint cover 20 as it is contemplated that a length of the securing members 28 may differ. Additional details regarding the shape and positioning of the splinting member 38 and the securing members 28 of the IV splint cover 20 will be provided below.

The main body 22 and the securing members 28 of the IV splint cover 20 according to an embodiment of the present invention may advantageously be integrally formed as a monolithic unit. This advantageously enhances ease of manufacture, and decreases costs associated with manufacture. Those skilled in the art will appreciate, however, that the IV splint cover 20 according to the present invention may advantageously be manufactured by connecting the securing members 28 to the main body 22 so that the securing members 28 and the main body 22 are separate structural members that are joined together. The description of the IV splint cover 20 being integrally formed as a monolithic unit should not be read as limiting, but is meant to illustrate one advantageous configuration of the present invention.

In one embodiment of the IV splint cover 20 according to the present invention, the bottom portions 32 of the pair of opposing securing members 28 may have an adhesive material 42 applied thereto. Similarly, the bottom portion 26 of the main body 22 that does not carry the splinting member 38 may have an adhesive material 40 applied thereto. It is important for the reader to appreciate that the embodiment of the IV splint cover 20 of the present invention that uses the adhesive 40, 42 in connection with the main body 22 and the securing members 28 does not have any adhesive applied to the bottom portion 26 of the main body 22 where the splinting member 38 is positioned over the IV site 90. This advantageously allows for the IV site 90 to be readily visualized by a medical professional, for example, or anyone that may have a need to visualize the IV site 90 on the patient. This is also advantageous to enhance comfort of the patient while the IV splint cover 20 according to an embodiment of the present invention is applied to the patient. More specifically, removal of the IV splint cover 20 from the extremity of the patient upon completion of the IV treatment may be made more comfortable when an adhesive is not included on the splinting member 38. Additional details regarding the advantages of being able to readily visualize the IV site 90 of the patient when using the IV splint cover 20 according to embodiments of the present invention are discussed below.

Figure 13:
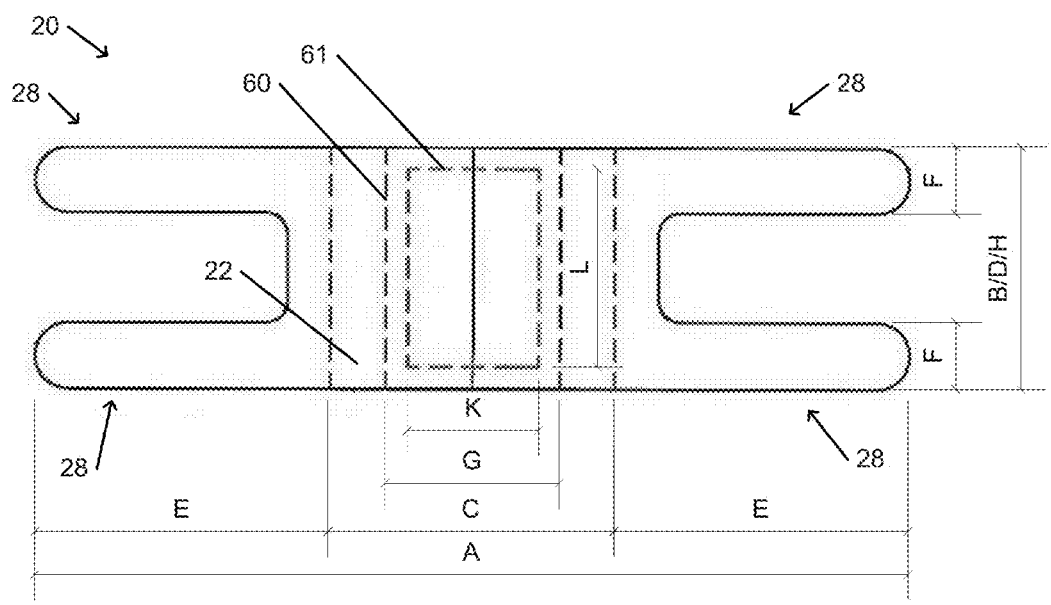
FIG. 13 is another bottom plan view of the intravenous splint cover illustrated in FIG. 1.
Figure 14:
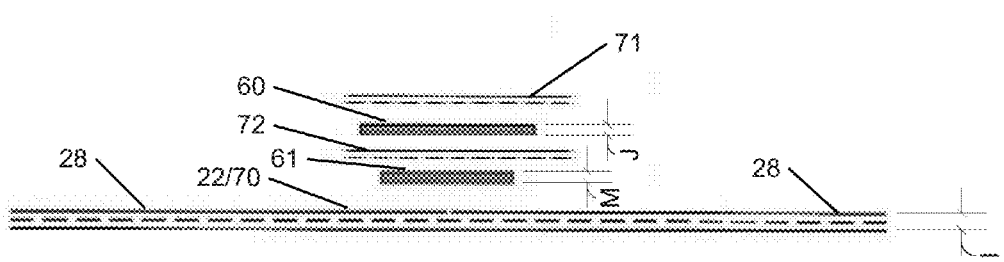
FIG. 14 is a side elevation view of the intravenous splint cover illustrated in FIG. 13.
Figure 15:
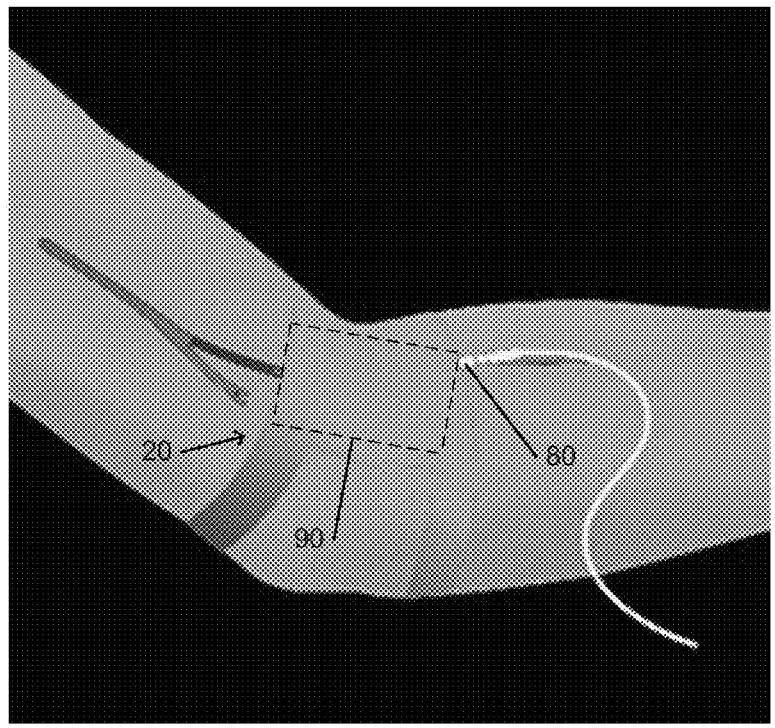
FIG. 15 is an environmental view of the intravenous splint cover illustrated in FIG. 1 positioned over an intravenous site on an extremity of a patient wherein the patient's extremity is straight.
Figure 16:
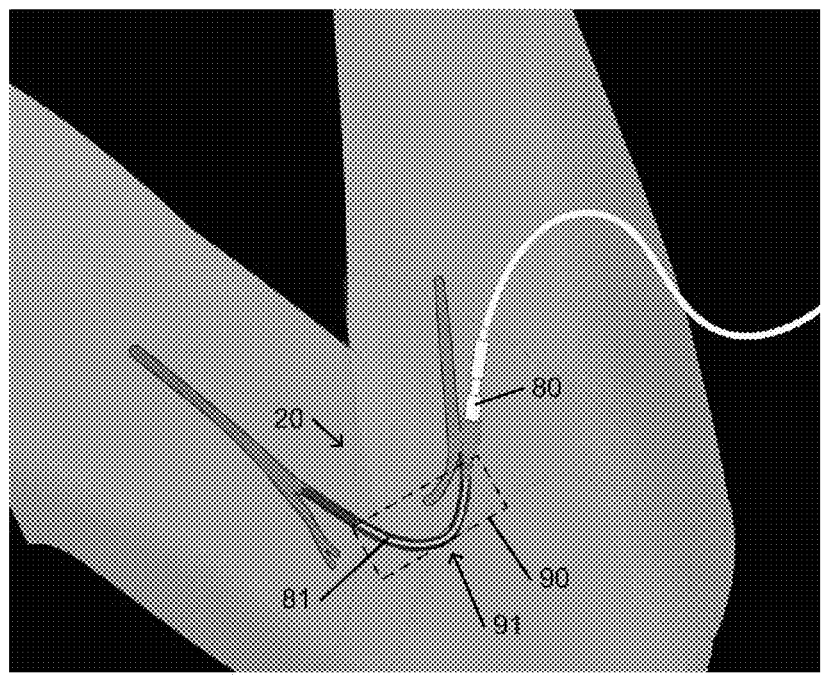
FIG. 16 is an environmental view of the intravenous splint cover illustrated in FIG. 1 as it is being positioned over an intravenous site on an extremity of a patient, and illustrated in a transparent fashion so as to show the patient's extremity being bent.
Figure 17:
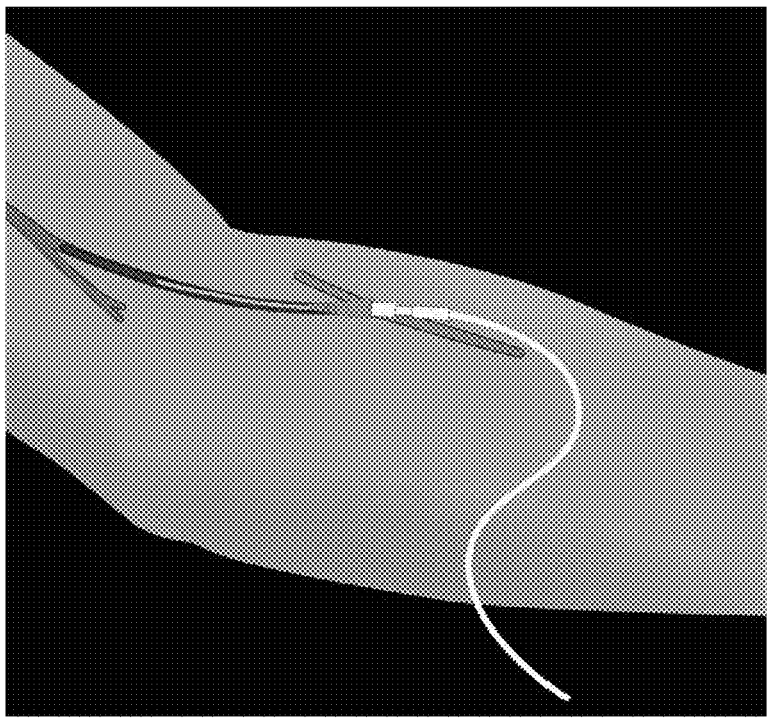
FIG. 17 is an environmental view of the intravenous site and an extremity of a patient without the intravenous splint cover wherein the patient's extremity is straight according to the prior art.
Figure 18:
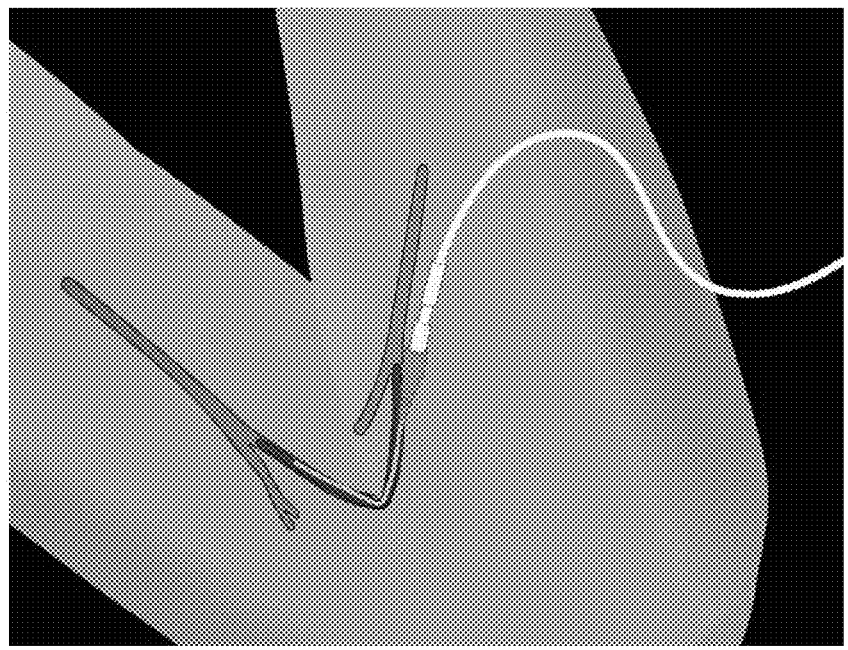
FIG. 18 is an environmental view of the intravenous site and an extremity of a patient without the intravenous splint cover wherein the patient's extremity is bent according to the prior art.

Referring now more specifically to FIGS. 13 and 14, the adhesive 40 may be applied to the main body 22 and may also allow the splinting member 38 to be secured to the main body 22. Additionally, the main body 22 may include a first and second main body 70, 71. The splinting member 38 may be placed on the first main body 70 and the second main body 71 may be placed on the splinting member 38. The adhesive 40 may be used to secure the splinting member 38 to the first main body 70 and the second main body 71 to the splinting member 38 and/or the first main body 70. The adhesive 40 may be used to secure the splinting member 38 and/or the first and/or second main body 70, 71 to each other or as otherwise desired. Those skilled in the art will appreciate that any number of methods, materials, and/or devices may be used to secure the splinting member 38 and/or the first and/or second main body 70, 71 including, but not limited to, adhesives, stitching or sewing, glue, fasteners, screws, bolts, welding (including ultrasonic welding), or any other means.

The adhesive material 42 that may be applied to the bottom portions 32 of the securing members 28 may have stronger adhesive properties than the adhesive material 40 that is applied to the bottom portion 26 of the main body 22. This may advantageously enhance the ability of the IV splint cover 20 to be readily secured to the IV site 90 on the patient. More specifically, providing a stronger adhesive on the securing members 28 may advantageously allow for the securing members to be readily secured to the skin of the patient when using the IV splint cover 20 according to an embodiment of the present invention. Further, using an adhesive 40 on the portion of the main body 22 (the portion that does not include the splinting member 38) that is weaker than the adhesive 42 used on the securing members 28 may advantageously enhance comfort of the patient when the IV splint cover 20 is applied to the IV site 90. In other words, when removing the IV splint cover 20, a patient may experience less discomfort adjacent to the IV site through the use of a weaker adhesive on the portions of the main body 22 where the splinting member 38 is not positioned.

Figure 3:
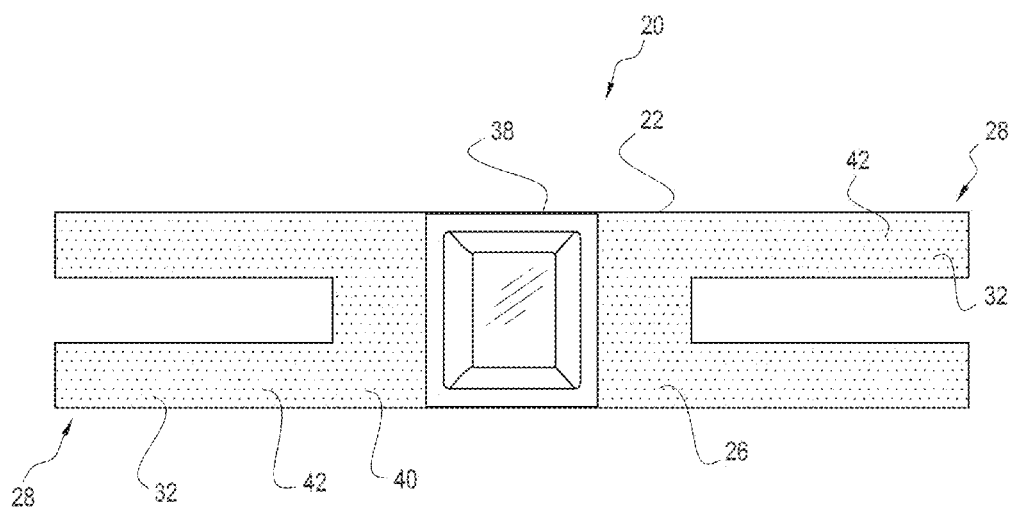
FIG. 3 is a bottom plan view of the intravenous splint cover illustrated in FIG. 1.
Figure 4:
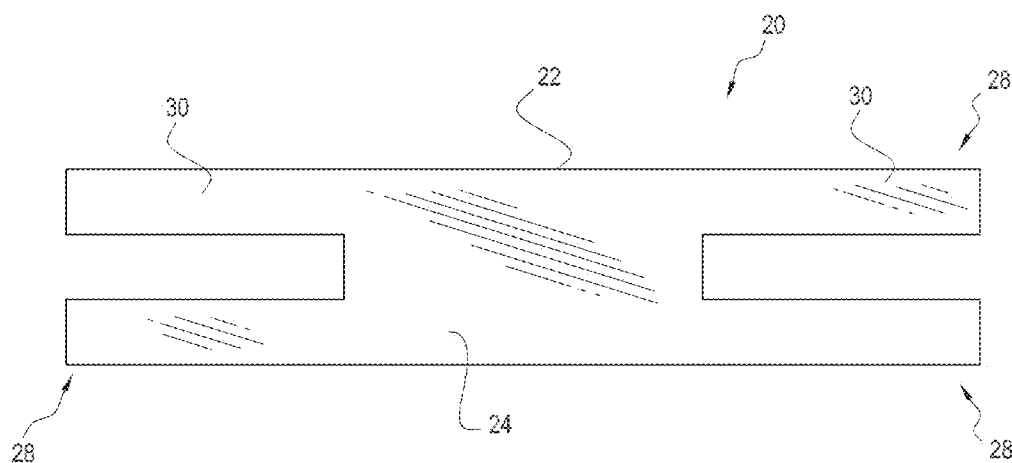
FIG. 4 is a top plan view of the intravenous splint cover illustrated in FIG. 1.
Figure 9:
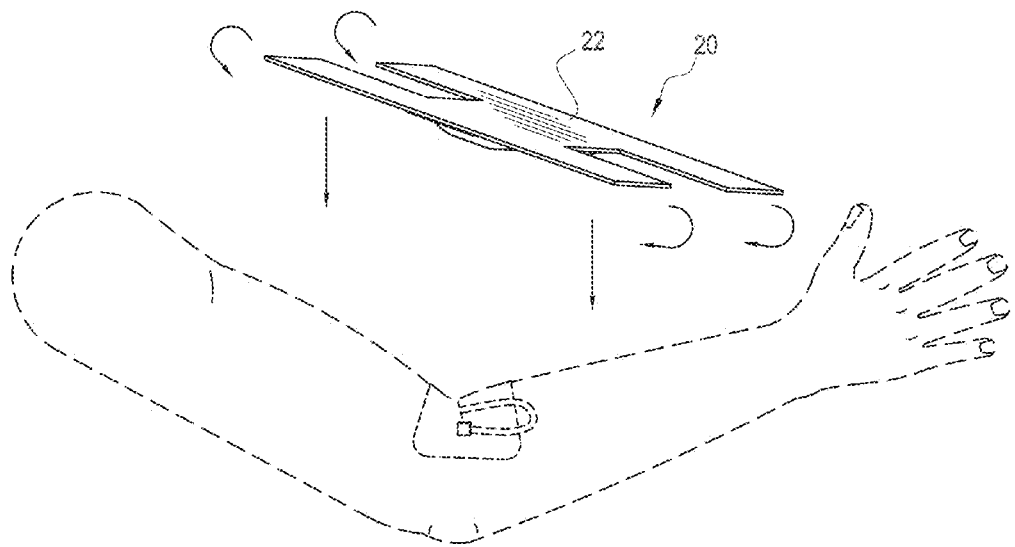
FIG. 9 is an environmental view of the intravenous splint cover illustrated in FIG. 1 as it is being positioned over an intravenous site on an extremity of a patient.
Figure 11:
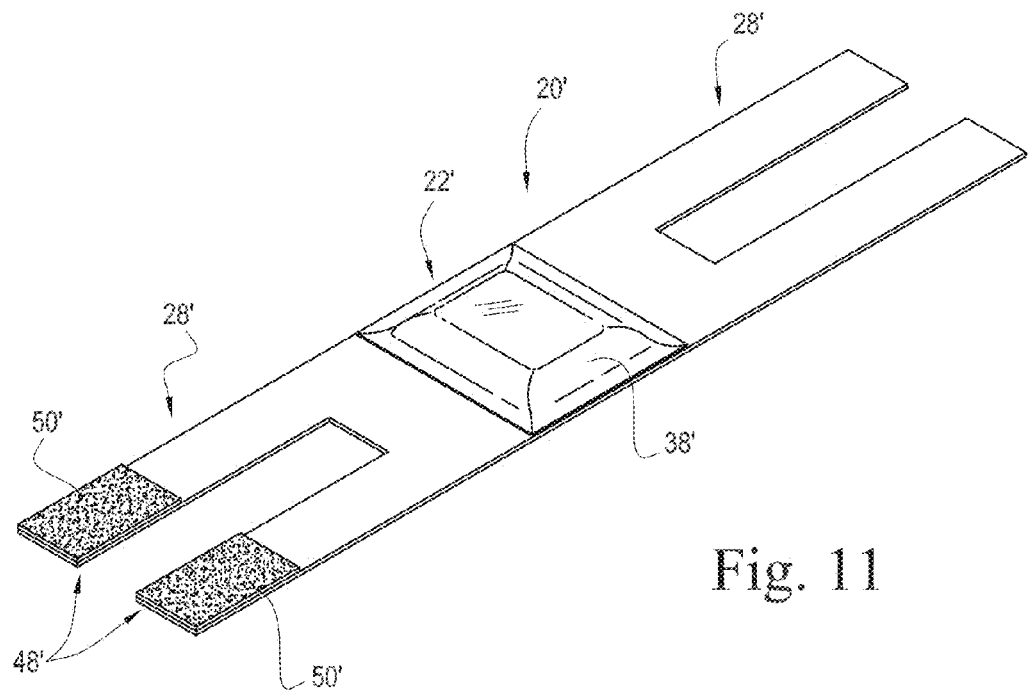
FIG. 11 is a perspective view of an intravenous splint cover according to an embodiment of the present invention.

The splinting member 38 may extend along the bottom portion of the main body 22 substantially between the entire width thereof. More specifically, and as perhaps best illustrated in FIGS. 1 and 3, substantially the entire splinting member 38 may extend the entire width of the main body 22, but the elevated portion of the splinting member 38 may taper from an elevation that is about equal to or higher than the bottom portion 26 of the main body 22, to a pinnacle thereof. Accordingly, and as perhaps best illustrated in FIG. 1, the splinting member 38 may advantageously taper downwardly from the pinnacle to the main body 22 on four sides in a trapezoidal shape. Those skilled in the art will readily appreciate, however, that any description of the shape of the splinting member 38 is not meant to be limiting in any way and, instead, are provided as examples for clarity. The splinting member 38 may have a rectangular shape, as shown in the figures. A rectangular shaped splinting member 38 may advantageously be easy to manufacture and package, and may provide enhanced convenience in storing and transporting, i.e., in boxes and with respect to shelf space. A rectangular shaped splinting member 38 may also be advantageous to overlap with an IV site 90 plastic cover. Such covers are generally clear, and have a rectangular shape. Other alternate shapes of the splinting member 38 may, for example, be circular, square, ovular, or any other type of shape suitable for being carried by a medial portion of the main body 22. As illustrated in FIG. 11, one embodiment may include the splinting member having a longitudinal and latitudinal profile with a bell curved frustum shape.

As best illustrated in FIGS. 13-14 (not necessarily drawn to scale), the IV splint cover 20 may vary in size due to several factors, including, but not limited to, the size of the patient, the sex of the patient, the age of the patient, and the type of extremity or body part that the device will be adhered to on the patient. For example, and without limitation, the overall length of the IV splint cover 20 "A" including the securing members 28 and the main body 22, may be approximately 3.0 to 16.0 inches and preferably about 10 inches. The overall width of the IV splint cover 20 "B" may be approximately 15-50% of the overall length of the IV splint cover 20 and preferably about 2.75 inches. The length of the main body 22 "C" may be approximately 0.5 to 6.0 inches and preferably about 3.25 to 4.25 inches. The width of the main body 22 "D" may be about equivalent to the overall width of the IV splint cover 20. The length of each securing member 28 "E" may be approximately 5-25% of the overall length of the IV splint cover 20 and preferably about 2.875 inches. The width of each securing member 28 "F" may be approximately 15-50% of the overall width of the IV splint cover 20 and preferably about 0.75 inches. The length of the splinting member 38 "G" may be approximately 0.5 to 6.0 inches and preferably about 1.5 to 2.0 inches. The width of the splinting member 38 "H" may be approximately 15-50% of the overall length of the IV splint cover 20 and preferably about 2.25 to 2.75 inches. The thickness of the main body 22 and the securing members 38 materials "I" may be approximately 0.005 to 0.25 inches and preferably about 0.011 inches. The thickness of the splinting member 38 "J" may be approximately 0.0625 to 1.0 inches and preferably about 0.125 inches. Those skilled in the art will appreciate that these dimensions may be increased or decreased as desired and the dimensions stated herein provided are exemplary.

For example and without limitation, some of the lengths, widths, and/or thicknesses may be substantially similar to one another. Substantially similar may indicate that the first measurement may be within a range of 80% to 120% of the second measurement. In addition, some of the lengths, widths, and/or thicknesses may be about a measurement. About may indicate that the actual measurement may be within a range of 80% to 120% of the specific measurement.

The splinting member 38 may be made of a substantially soft and pliable material. For example, the splinting member 38 may include a foam type of material, a cotton splint material, a plastic material, a metallic material, a metal-alloy material, a ceramic material, a polymer material, other similar material, or any combination thereof. For example, and without limitation, the splinting member 38 may be a crosslinked polyethylene foam coated on one side with an acrylic based, hypoallergenic pressure sensitive adhesive. The acrylic and/or stretchable based, porous, breathable, and/or hypoallergenic pressure sensitive adhesive may be protected by a polycoated white kraft release liner. Cotton materials may be preferable to form the splinting member as it may provide enhanced rigidity, and may be more suitable for patients that have allergies to various materials. The use of such material advantageously enhances comfort of the IV splint cover 20 when applied to the IV site 90 of the patient. Such material may also advantageously have certain absorption properties that can be advantageous to soak minor amounts of blood, fluid, or medication leaks that may be associated with the use of an IV. Comfort of the patient is one of the several advantages provided by the IV splint cover 20 according to the present invention, and those skilled in the art will appreciate that the splinting member 38 may be made of any other similar material that provides enhanced comfort to the patient when applied to the IV site 90. In addition, the splinting member 38 material may be more rigid than the main body 22 material and/or the securing members 28 material.

The splinting member 38 may include a first splinting member 60 and a second splinting member 61. The first splinting member 60 may include a foam type of material, a cotton material, a plastic material, a metallic material, a metal-alloy material, a ceramic material, a polymer material, other similar material, or any combination thereof. The first splinting member 60 may preferably be a cotton material such as a nonwoven tape. The second splinting member 61 may include a foam type of material, a cotton material, a plastic material, a metallic material, a metal-alloy material, a ceramic material, a polymer material, other similar material, or any combination thereof. The second splinting member 61 may preferably be a foam type of material. For example, and without limitation, the second splinting member 61 may be a crosslinked polyethylene foam coated on one side with an acrylic based, hypoallergenic pressure sensitive adhesive. The acrylic based, hypoallergenic pressure sensitive adhesive may be protected by a polycoated white kraft release liner.

The second splinting member 61 may attach to the main body 22. The first splinting member 60 may attach to the main body 22 and/or the second splinting member 61. The first splinting member 60 may be larger than the second splinting member 61. For example and without limitation, the first splinting member 60 may be about 2.0 inches long and about 2.750 inches wide and the second splinting member 61 may be about 1.5 inches long and about 2.25 inches wide.

The adhesive 40 may be applied to the main body 22 and may also allow the first and second splinting members 60, 61 to be secured to the main body 22. The main body 22 may include, in addition to the first and second main body 70, 71, a third main body 72. The second splinting member 61 may be placed on the first main body 70, the third main body 72 may be placed on the second splinting member 61 and/or the first main body 70, the first splinting member 60 may be placed on the third main body 72, the second splinting member 61, and/or the first main body 70, and the second main body 71 may be placed on the first splinting member 60, the third main body 72, the second splinting member 61, and/or the first main body 70. The adhesive 40 may be used to secure the first and/or second splinting member 60, 61 and/or the first, second, and/or third main body 70, 71, 72 to each other or as otherwise desired. Those skilled in the art will appreciate that any number of methods, materials, and/or devices may be used to secure the first and/or second splinting member 60, 61 and/or the first, second, and/or third main body 70, 71, 72 including, but not limited to, adhesives, stitching or sewing, glue, fasteners, screws, bolts, welding (including ultrasonic welding), or any other means.

As best illustrated in FIGS. 13-14, the length of the first splinting member 60 "G" may be approximately 0.5 to 6.0 inches and preferably about 2.0 inches. The width of the first splinting member 60 "H" may be approximately 15-50% of the overall length of the IV splint cover 20 and preferably about 2.75 inches. The thickness of the first splinting member 60 "J" may be approximately 0.0625 to 1.0 inches and preferably about 0.125 inches. The length of the second splinting member 61 "K" may be approximately 0.5 inches to 6.0 inches and preferably about 1.5 inches. The width of the second splinting member 61 "L" may be approximately 15-50% of the overall length of the IV splint cover 20 and preferably about 2.25 inches. The thickness of the second splinting member 61 "M" may be approximately 0.0625 to 1.0 inches and preferably about 0.125 inches. Those skilled in the art will appreciate that the length of the first and second splinting members 60, 61 may be equal to the full length of the main body 22. The width of the first and second splinting members 60, 61 may be equal to the full width of the main body 22.

As perhaps best illustrated in FIG. 1, each of the pair of opposing securing members 28, i.e., each of the securing members 28 on either side of the main body 22 of the IV splint cover 20, may include a pair of securing members 28. More specifically, and with specific reference to FIGS. 1 and 2, the securing members 28 may be spaced apart from one another and extend outwardly from the main body 22 substantially parallel to one another. The securing members 28 on either end of the main body 20 may be considered symmetrical to one another. The present invention contemplates, however, that the securing members 28 on either end of the main body 22 of the IV splint cover 20 may have different lengths or may have similar lengths. Application of the of the IV splint cover 20 may, in some instances be facilitated if the securing members 28 on one end of the main body 22 have a length that is greater than the securing members 28 on the opposing end of the main body 22. Again, this may be an optional feature, and the skilled artisan will appreciate that any length of the securing members 28 of the IV splint cover 20 according to an embodiment of the present invention is contemplated by the present invention.

Although the embodiment of the IV split cover 20 illustrated in the appended figures shows the use of a pair of securing members 28 on either side of the main body 22, those skilled in the art will appreciate that any number of securing members 28, configured in any way, may be provided while still carrying out the many different goals, features and advantages according to the present invention. For example, the illustrated embodiment of the IV splint cover 20 shows a pair of securing members 28 extending parallel to one another outwardly from each side of the main body 22, but those skilled in the art will appreciate that the securing members 28 do not need to necessarily extend parallel to one another out from the main body 22. In fact, the securing members 28 may extend in any direction, e.g., diagonally. Further, although a pair of securing members 28 is illustrated on either side of the main body 22, the present invention contemplates that more than two securing members 28 may be used to carry out the many different goals and features of the present invention. More specifically, it is contemplated that three securing members 28 may extend outwardly from the main body 22 of the IV splint cover 20. Such a configuration may advantageously provide enhanced security of the IV splint cover 20 according to the present invention when applied to the IV site 90 of a patient. It should be noted, however, that the illustrated embodiment of the IV splint cover 20 does advantageously provide for enhanced security of the IV site 90 of the patient while simultaneously providing the patient with ease of mobility of the extremity where the IV site 90 is positioned. For example and without limitation, if the catheter 81, needle, cannula, flexible tube, etc. is or has been inserted in the cubital fossa, also known as the elbow pit or antecubital fossa, the IV splint cover 20 may allow a patient to bend, or bend further, his or her arm at the elbow. With the IV splint cover 20 in place, damage to the patient caused by bending of the arm of the patient may be reduced or negated. With the IV splint cover 20 in place, kinking, shifting, dislodging or blockage of the IV line 80 may be reduced or negated, thus allowing for continued IV therapy 91. Thus, the patient may have increased mobility when the IV splint cover 20 is used as opposed to when the IV splint cover is not used. For example and without limitation, the wrist may be able to bend and the forearm may be able to rotate and/or pivot as desired when the IV splint cover 20 is attached to the wrist and forearm, respectively.

The material that the IV splint cover 20 according to an embodiment of the present invention may be made of, i.e., the main body 22 and the securing members 28, may be a disposable material that is preferably biodegradable. Such materials are readily known in the art. For example and without limitation, the main body 22 and securing member 38 materials may be polyurethane and the adhesive materials 40, 42 may be acrylate. Using such material is advantageous to reduce waste. Those skilled in the art will appreciate that the main body 22 and the securing members 28 of the IV splint cover 20 may, however, be made of any type of material, while still readily achieving the many different goals and features according to the present invention. It is also preferable that the material of the IV splint cover 20 be substantially flexible with at least some rigidity and/or stretchability. Using such material enhances application of the IV splint cover 20 to the IV site 90 of the patient. As will be discussed in greater detail below, application of the IV splint cover 20 to the IV site 90 of the patient can be accomplished in a one step process. This one step process is enhanced when using a flexible and/or stretchable material to form the main body 22 and the securing members 28 of the IV splint cover 20.

It is also preferable that all material used to construct the IV splint cover 20 according to the present invention is made of a pressure sensitive, porous, breathable and/or hypoallergenic material. Although it is readily understood that constructing the IV splint cover 20 out of such material may be a more costly approach, it is preferable to provide an IV splint cover that can be readily used for all patients. Those skilled in the art, however, will appreciate that the IV splint cover 20 may be readily made of any material, and that use of a hypoallergenic material is an available option contemplated by the present invention. The IV splint cover 20 according to the present invention may also be made of a latex free material to further account for possible allergies of a patient. Again, those skilled in the art will appreciate that any material may be used to construct the IV splint cover 20, but the present invention readily contemplates use of such materials to account for possible allergies that patients may have. Although many patients may be allergic to certain types of materials, the present invention contemplates using paper types of materials to construct the IV splint cover 20.

The material that may be used to construct the IV splint cover 20 may also have a color that is similar to the skin tone of the patient. This is advantageous for many reasons. Although it may seem that having an IV splint cover 20 with a color that is similar to the skin tone of the patient is merely aesthetic, those skilled in the art will appreciate that using an IV splint cover 20 having a color similar to the skin tone of the patient is advantageous as it can hide the IV splint cover from view of the patient. This may be especially advantageous when using the IV splint cover 20 on patients that may be easily confused. Such patients may desire to rip the IV out, and use of the IV splint cover 20 according to the present invention may hide the IV from site of such patients, thereby detracting attention from it.

A portion of the IV splint cover 20 may be lifted so that a medical professional may view the IV site 90, the catheter 81, needle, cannula, flexible tube, etc., or the IV line 80, or any portion thereof, without the need for removing the IV splint cover 20. For example and without limitation, the splinting member 38 and the top portion 24 may be lifted so that the IV site 90 or a portion thereof may be viewed. The bottom portions 32 of the securing members 28 may remain adhered to the patient while the splinting member 38 and the top portion 24 are lifted. The ability to stretch, lift, view, and/or assess a portion of the IV splint cover 20 will keep the IV site 90 covered so that a patient still cannot view the IV site 90, the catheter 81, needle, cannula, flexible tube, etc., or the IV line 80, or portions thereof, yet still allow a medical professional to view the IV site 90, the catheter 81, needle, cannula, flexible tube, etc., or the IV line 80, or any portion thereof, when desired or necessary. For example and without limitation, a user may grasp a center portion of the splinting member 38, which may be non-adhesive, with fingers to stretch, lift, view, and/or assess the IV site 90. Once the splinting member 38 is released, it may return to its previous form and may keep the IV site 90 covered so that a patient cannot view the IV site 90, the catheter 81, needle, cannula, flexible tube, etc., and/or at least a portion of the IV line 80.

Thus, the IV site 90 may remain accessible to a user to be able to assess, palpate, and visualize the IV site 90 at any time. The IV site 90 may be easily viewed or palpated from the top or bottom without removing the IV splint cover 20. The IV splint cover 20 may remain on the patient over the IV site 90 without the splinting member 38 adhering to or removing the existing intact IV site 90. For example, and without limitation, to view the insertion site and/or the IV site 90 a user may grasp a portion of the IV splint cover 20, such as the splinting member 38, by lifting the portion of the IV splint cover 20 along the side edge of the IV splint cover 20. As another example, and without limitation, a user may lift and stretch a portion of the IV splint cover 20 from the top edge or bottom edge of the splinting member 38. These examples may allow a user to view or palpate the IV site 90 underneath the IV splint cover 20 as desired. The IV splint cover 20 may stretch by lifting, but may return to its original form or generally its original form to conform to the IV site 90 allowing the splint cover 20 to return to the function of allowing mobility of the patient's extremity by splinting the IV site 90 and preventing kinking, shifting, blocking, damage or dislodgement of the catheter 81, needle, cannula, flexible tube, etc. Thus, the patient may be free or freer to move his or her extremity or joint to completely pivot and continue pivoting during IV therapy 91 without the need for immobilization of a joint or extremity.

Furthermore, the IV site 90 may be easy to visualize, access, and/or palpate without compromising the IV site 90 while protecting it underneath as the IV splint cover 20 remains intact over the IV site 90. By further preserving the IV site 90, users may be less invasive and the risk of introduction of infection from IV reinsertion may be reduced. The IV splint cover may be applied in a one step process and may be easy to use, comfortable, hypoallergenic, camouflaging, inexpensive to make, disposable, and environmentally friendly.

The IV splint cover 20 may be made of a material that is flexible and/or capable of stretching so that when the IV splint cover 20, or a portion thereof, is lifted, the IV splint cover 20 may generally maintain its position, shape, and/or size. This flexibility may allow the IV splint cover 20 to retain its form for support and continue to allow a patient to have mobility in his or her extremities.

At least a portion of the IV splint cover 20 is made of a stretch material allowing for flexibility and bending. The splinting member 38 may be an elevated cushion pad in the center of the IV splint cover 20 which is designed to splint, support and protect the catheter 81, needle, cannula, flexible tube, etc. The splinting member 38 may have the ability to stretch, but maintain enough rigidity and retain or nearly retain its form for splinting the IV site 90 with the ability to allow complete or nearly complete movement and pivoting when a joint or extremity moves Application of the IV splint cover 20 may be accomplished by pulling a pair of adhesive cover members 44 and applying one self-adhesive side at a time in one motion with the splinting member 38 centered over the IV site 90. The two securing members 28 may adhere to the patient's skin on each end parallel to each other and may wrap around the extremity or joint adhering to the skin and allowing for the extremity or joint to have free or generally free range of motion. Once applied, the securing members 28 may stretch with the extremity or joint when the extremity or joint moves and may work together with the stretch ability of the splinting member 38. The IV splint cover 20 may be used on all patients. By covering, protecting, and splinting the IV site 90, a user may have more comfort and the IV site 90 may be concealed from the patient's view which may be especially beneficial to patients who are needle-phobic, infants, children, confused, and/or agitated patients while still allowing the ability for total joint or extremity flexion, IV site 90 access, and IV therapy 91.

The securing members 28 may be applied above and below the joint to allow bending of any joint by stretching with the joint and or extremity when the joint or extremity moves. A user may pull the pair of adhesive cover members 44 in one motion allowing the securing members 28 to adhere to the patient's skin. When the securing members 28 are wrapped around a joint or extremity, the securing members 28 may contour above and below the joint which may allow for bending and flexibility of the extremity or joint. The securing members 28 may overlap on the ends but do not need to overlap to allow a patient to move and bend more freely. The placement and ability of the securing members 28 to stretch yet retain their form by conforming to an extremity or joint may help to promote blood flow without causing a tourniquet effect. Once the securing members 28 are applied to the joint or extremity, the joint or extremity may bend while the securing members 28 may stretch and may allow for continued mobility and pivoting of an extremity or joint and thus allowing movement without the need for immobilizing of the joint or extremity which may otherwise impede blood flow and circulation.

It may also be advantageous to provide a material for the main body 22 and the securing members 28 that is waterproof or water resistant. This advantageously allows a patient to bath or shower while the IV splint cover 20 is applied to the IV site 90. Accordingly, the IV splint cover 20 according to embodiments of the present invention not only allows the patient's extremity to remain mobile while in use, but also advantageously enhances the ability of the patient to engage in other routine daily activities while IV medical treatments are being administered. Further, the IV splint cover 20 is advantageous for patients that are receiving multiple IV treatments, i.e., use of the IV splint cover prevents immobilization of the patient's extremities, which can be especially advantageous for patients that may have IV's in two different extremities.

Figure 10:
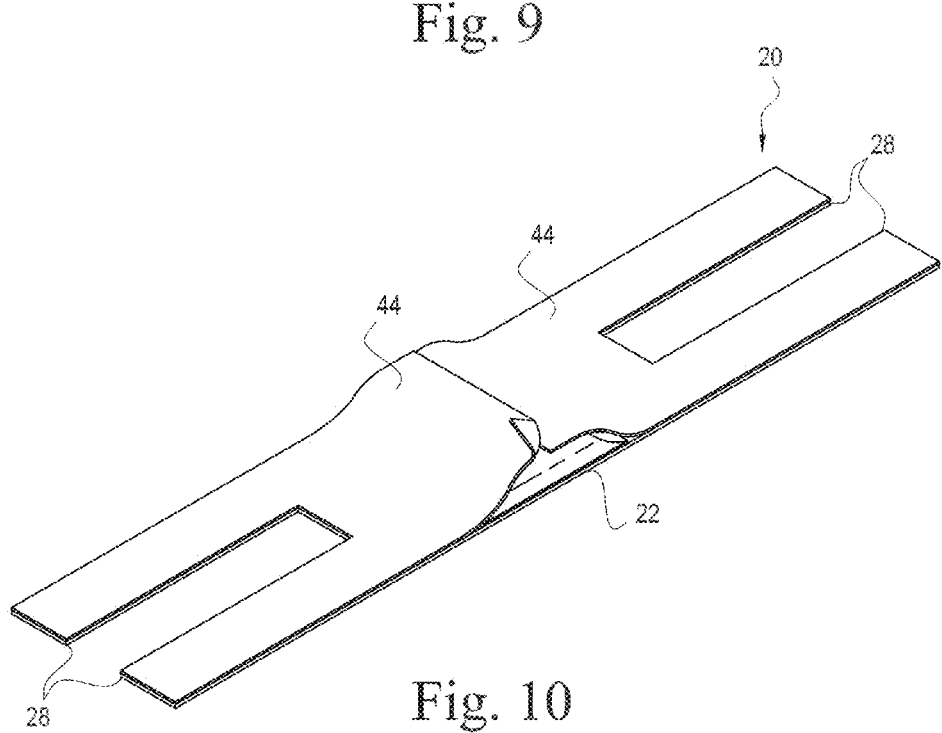
FIG. 10 is a perspective view of an intravenous splint cover according to an embodiment of the present invention showing a pair of adhesive cover-members positioned over a bottom surface portion thereof.

As perhaps best illustrated in FIG. 10, the IV splint cover 20 according to the present invention may further include adhesive cover members 44 that may be removeably positioned over the main body 22 and the securing members 28. The adhesive cover members 44 are positioned to overlie the bottom portion 26 of the main body 22 and the bottom portion 32 of the securing members 28. Accordingly, the adhesive cover members 44 may readily protect the adhesive from exposure when not in use to ensure that the adhesive remains strong enough to be applied to a patient. As further illustrated in FIG. 10, the adhesive cover members 44 may be provided by a pair of adhesive cover members 44. A first one of the pair of adhesive cover members 44 may be positioned to extend from an end portion of one of the securing members 28 to a medial portion of the main body 22 of the IV splint cover 20, and a second one of the pair of adhesive cover members 44 may extend form an end portion of the opposing securing member 28 to the medial portion of the main body 22. Accordingly, the present invention contemplates that end portions of the adhesive cover members 44 may somewhat overlap adjacent the medial portion of the main body 22 so that the adhesive cover members 44 can be readily removed when used.

The adhesive cover members 44 may be made of a paper material, a paper-like material, a paper material having a plastic coating, or a plastic material to cover the portions of the main body 22 and the securing members 28 that have adhesive material applied thereto. The use of such materials for the adhesive cover members 44 advantageously allows for the adhesive cover members 44 to be readily connected to the adhesive portions of the main body 22 and the securing members 28 in a manner that allows the adhesive to remain protected from the elements, and that allows for the adhesive cover members 44 to be readily removed from the adhesive portions of the IV splint cover 20.

Figure 12:
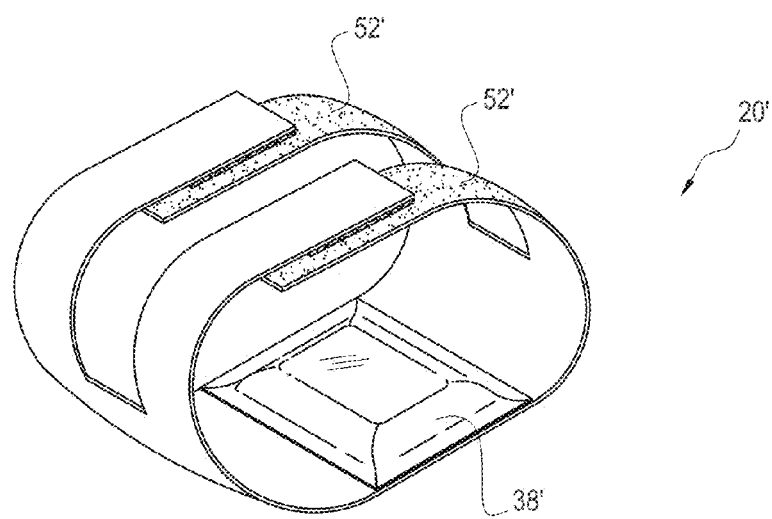
FIG. 12 is a perspective view of the intravenous splint cover illustrated in FIG. 11 showing securing members being connected to one another.

Referring now additionally to FIGS. 11 and 12, an alternate embodiment of the IV splint cover 20' is now discussed in greater detail. More specifically, the IV splint cover 20' may include a pair of opposing securing members 28' that are connected to and extend outwardly from the main body 22'. In this embodiment of the IV splint cover 20', fasteners 48' may be carried by end portions of each of the pair of securing members 28'. The fasteners 48' may include fasteners 50' positioned on the bottom side of the securing members 28' and fasteners 52' positioned on the top side of the securing members 28'. The fasteners 48' may be provided by hook and loop fasteners, as understood by those skilled in the art. The other elements of this embodiment of the IV splint cover 20' not specifically described herein are similar to those of the first embodiment of the IV splint cover 20 described above, are labeled with prime notations, and require no further discussion herein.

Referring now back to FIGS. 1 through 10, use of the IV splint cover 20 according to an embodiment of the present invention is now described in greater detail. When using the IV splint cover 20 according to an embodiment of the present invention, a user, such as, for example, a medical professional, may remove the IV splint cover 20 from a package. The packaging that contains the IV splint cover 20 is preferably a sterilized material to ensure that the IV splint cover 20 remains sterile during transport, however, the packaging and the IV splint cover 20 may not be sterilized or composed of sterilized material(s). The IV splint cover 20 may be sterile and therefore the material or materials that make up the IV splint cover 20 may also be sterile. This advantageously reduces the risk of infection to the patient when using the IV splint cover 20. Those skilled in the art will appreciate that although the packaging that houses the IV splint cover 20 is described herein, the function of the present invention can be readily carried out without the use of such packaging.

After the IV splint cover 20 according to the present invention has been removed from the packaging, the medical professional may remove the adhesive cover members 44 positioned to overlie the bottom portion 26 of the main body 22 and the bottom portion 32 of the securing members 28. Removal of the adhesive cover members 44 advantageously exposes the adhesive material 40, 42 positioned on the bottom portion 26 of the main body 22 and the bottom portion 32 of the securing members 28. Removal of the adhesive cover members 44 also advantageously exposes the splinting member 38. After the bottom portion of the main body 22 has been exposed, the medical professional may readily apply the IV splint cover 20 centered and/or over the IV site 90 of the patient. The securing members 28 may be adhered to the patient one side at a time with or without stretching. To inspect the IV site 90, the center portion of the splinting member 38, which may be non-adhesive, may be lifted to visualize the IV site 90.

Those skilled in the art will appreciate that the medical professional may completely remove the adhesive cover members 44 or may, alternatively, only remove enough of the adhesive cover members 44 to expose the splinting member 38. As described below, the securing members 28 can be applied directly to the skin of the patient adjacent to the IV site 90, if the adhesive cover members 44 are fully removed, or the adhesive cover members 44 can be removed as the securing members 28 are applied to the skin of the patient. In other words, the process of removing the adhesive cover members 44 and applying the securing members 28 to the skin of the patient can be a substantially simultaneous process. This advantageously allows for the adhesive material on the bottom portion 26 of the main body 22 and on the bottom portion 32 of the securing members 28 to remain covered until almost the instant that the main body 22 and the securing members 28 are to be applied to the IV site 90.

When applying the IV splint cover 20 to the IV site 90 of the patient, the medical professional, after starting the IV, may apply the splinting member 38 by centering it over the IV site 90. Application of the splinting member 38 to the IV site 90 may advantageously prevent the catheter 81, needle, cannula, flexible tube, etc. from bending when the patient bends their extremity. More particularly, the splinting member 38, after being applied over the IV site 90, keeps the catheter 81, needle, cannula, flexible tube, etc. from bending, but advantageously allows the extremity of the patient to bend, so that the patient can be comfortable while receiving IV treatments and can enjoy other routine daily activities. Thereafter, the securing members 28 may adhere in one motion, one side at a time over the extremity of the patient, and the adhesive material 40, 42 on the main body 22 and the securing members 28 may be applied to the skin of the patient. The splinting member 38 advantageously secures the IV site 90 so that the IV does not come out while the patient is receiving IV treatments. Further, application of the IV splint cover 20 to the extremity of the patient where the IV is located advantageously secures the IV while not immobilizing the patient's extremity. In other words, the patient may still readily move and bend the extremity where the IV is located while the IV remains secured while stretching with movement.

The configuration of the IV splint cover 20 according to embodiments of the present invention advantageously allows for application of the IV splint cover 20 in a one step process. This step can be described as simply applying the splinting member 38 to the IV site 90 by centering the splinting member 38 over the IV site 90 while connecting the securing members 28 to the skin of the patient adjacent to the IV site 90.

The configuration of the IV splint cover 20 according to the present invention also advantageously provides the medical professional with the ability to readily connect the IV splint cover 20 to the IV site 90 of the patient using one hand, which may sometimes be necessary in many medical settings. For example, after applying the splinting member 38 to the IV site 90 of the patient, the medical professional may hold the splinting member 38 securely on the IV site 90 using a thumb, fingers or hand, for example, and may move the securing members 28 over the side portions of the extremity (to either side of the IV site 90) so that the adhesive portions on the main body 22 of the IV splint cover 22 and on the securing members 28 contact the skin of the patient. After the IV splint cover 20 according to this embodiment of the invention is positioned over the IV site 90 of the patient, and since adhesive is not applied to portions of the main body 22 where the splinting member 38, which may be non-adhesive, is positioned and/or centered over the IV site 90, the IV site 90 may be readily visualized by the medical professional when the IV splint cover 20 is applied by grasping, for example, the top edge or bottom edge of the splinting member 38 with fingers then stretching and lifting the center portion of the splinting member 38 to assess and visualize the IV site 90.

It is preferable when applying the IV splint cover 22 to the IV site 90 on the patient, that the securing members 28 do not overlap one another at end portions thereof, however the securing members 28 may overlap one another at end portions thereof and may adhere to one another. More specifically, the medical professional may stretch the securing members 28 a distance suitable for the securing members 28 to overlap one another during application. Alternatively, the medical professional may place the securing members 28 on the skin of the patient with little or no stretching of the securing member 28. The securing members 28 may or may not overlap and may stretch upon movement of the patient, the patient's extremity, or otherwise as desired. It is also preferable for the securing members 28 to be applied to the skin of the patient adjacent the joint on the patient where the IV site 90 is positioned. This enhances mobility of the patient when the IV splint cover 20 is positioned over the IV site 90.

Referring now back to the embodiments of the IV splint cover 20' illustrated in FIGS. 11 and 12, another embodiment of the method of using the IV splint cover 20' is now described in greater detail. In this embodiment, the fasteners 48' positioned on the bottom portion of the securing members 50' and on the top portion of the securing members 52' may be configured to connect to one another. As described above, the fasteners 48' may be provided by hook and loop fasteners. Accordingly, and with reference to the illustrated embodiment of the IV splint cover 20', the securing members 28' that extend outwardly from a first side of the main body 22' may have fasteners 50' positioned on a bottom portion thereof, and the securing members 28' extending from the opposing side of the main body 22' may have fasteners 52' positioned on a top portion thereof. After the medical professional has applied the splinting member 38' to the IV site 90', the securing members 28' may be placed and/or stretched over the extremity of the patient, and the securing members 28' may be connected to one another so that the fasteners 48' may be connected to one another.

Some additional features of the IV splint cover 20 are now described in greater detail. One option that is contemplated by the present invention is to make the IV splint cover 20 child friendly. This can be accomplished by positioning indicia that is child related on the top portion of the main body 22 and the securing members 28. The indicia may, for example, be directed to children's characters, or any other type of indicia that may be pleasing to children. This advantageously directs children's attention away from the IV site 90, and may focus the children's attention on the characters that are printed on the IV splint cover 20. The IV splint cover 20 according to the present invention also contemplates that the main body 22 and securing members 28 may be very brightly colored, which may also detract a child's attention from the IV site 90.

The splinting member 38 may completely cover the IV site 90 or a portion of the IV site 90. For example, and without limitation, the splinting member 38 may be positioned over the inserted portion of the catheter 81, needle, cannula, flexible tube, etc. that is beneath the skin of the patient. As another example, and without limitation, the splinting member 38 may be positioned over the entire length of the catheter 81, needle, cannula, flexible tube, etc. including the inserted portion beneath the skin of the patient as well as the portion above the skin of the patient. The positioning of the splinting member 38 may prevent or aid in preventing the catheter 81, needle, cannula, flexible tube, etc. from bending, breaking, kinking, shifting or dislodging.

As another embodiment of the IV splint cover 20, a method of using the IV splint cover 20 may also be used. In the method, the IV splint cover 20 may include a main body 22 that may have a rectangular shape and may include a bottom portion 26 and a top portion 24. The IV splint cover 20 may further include a pair of opposing securing members 28 that may have a rectangular shape and may be connected to and may extend outwardly from the main body 22 and may include a bottom portion 32 and a top portion 30. The IV splint cover 20 may also include a splinting member 38 that may have a rectangular shape and may be carried by the bottom portion 26 of the main body 22 and may extend outwardly from the main body 22 to create an elevated portion of the main body 22. The IV splint cover 20 may yet further include a pair of adhesive cover members 44.

The method may include removing a portion of the pair of adhesive cover members 44 so that an adhesive side of one set of opposing securing members 28 and a portion of the main body 22 may be exposed. The method may further include positioning the splinting member 38 over an IV site 90 and securing the one set of opposing securing members 28 and the portion of the main body 22 to skin of a patient. The method may also include removing the opposing portion of the pair of adhesive cover members 44. The method may still further include securing the opposing set of opposing securing members 28 and the opposing portion of the main body 22 to another portion of the skin of the patient or to the set of opposing securing members 28. Those skilled in the art will appreciate that the methods herein may be performed in an interchangeable order. Further, those skilled in the art will appreciate that multiple adhesive cover members 44 may be removed at or near the same time, thus exposing the adhesive side of the securing members 28. With multiple adhesive cover members 44 removed, a user may position the splinting member 38 over the IV site 90 and secure the securing members 28 and the portions of the main body 22 to skin of the patient.

The bottom portions of the pair of opposing securing members 28 may have an adhesive material 42 applied thereto. The bottom portion 26 of the main body 22 that does not carry the splinting member 38 may have an adhesive material 40 applied thereto. The main body 22, the securing members 28, and/or the splinting member 38 may comprise a flexible material whereby an IV site 90 may be covered by the IV splint cover 20 unless the main body 22, the securing members 28, and/or the splinting member 38 is/are expanded.

An overall width of the IV splint cover 20 may be about 50% or less than an overall length of the IV splint cover 20. A length of the main body 22 may be about 50% or less than the overall length of the IV splint cover 20. A width of the main body 22 may be substantially equal to the overall width of the IV splint cover 20. A length of each securing member 28 may be about 25% or less than the overall length of the IV splint cover 20. A width of each securing member 28 may be about 50% or less than the overall width of the IV splint cover 20. A length of the splinting member 38 may be less than a length of the main body 22. A width of the splinting member 38 may be less than a width of the main body 22. Those skilled in the art will appreciate that these dimensions may be increased or decreased as desired and the dimensions stated herein provided are exemplary. For example and without limitation, the dimensions may be increased or decreased relative to the size of the IV site 90 or the body part.

Additional advantages are apparent with respect to the IV splint cover 20 according to the present invention. For example, use of the IV splint cover 20 results in a substantial decrease in costs associated with medical care. This is realized from costs saved in additional medical supplies associated with reinsertion of the IV, and also from a decrease in labor costs associated with the medical staff that would otherwise need to reinsert the IV. Reinsertion of the IV may also expose a patient to infection and additional and/or increased medical costs. There is also an inherent cost associated with patient comfort. Patients that do not require reinsertions of IV's are generally more comfortable, more satisfied, and can generally heal quicker, thereby decreasing inherent medical costs associated with prolonged recovery times. In addition, the IV splint cover 20 will make it more difficult to kink, shift or dislodge the IV line 80. As a result, there will be less chance for improper or delayed medication delivery or other fluids which a patient requires or as otherwise desired by medical staff to be provided to the patient to increase patient healing and decrease medical costs.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An intravenous splint cover comprising:
   a main body having a rectangular shape, the main body comprising a bottom portion,
   a top portion,
   a first side, and
   a second side,
   a first pair of securing members that have a rectangular shape and connect to and extend outwardly from the main body comprising:
   a first securing member, and
   a second securing member,
   wherein the first securing member and the second securing member extend outwardly from the first side of the main body in parallel along an entire length of each of the first and second securing members;
   a second pair of securing members extending outwardly from the second side of the main body and comprising:
   a third securing member, and
   a fourth securing member,
   wherein the third securing member and the fourth securing member extend outwardly from the second side of the main body in parallel along an entire length of each of the third and fourth securing members;
   a splinting member comprising a longitudinal and latitudinal profile with a bell curved frustum shape and is carried by the bottom portion of the main body and extends upwardly from the main body to create an elevated portion of the main body;
   wherein the splinting member comprises an undulated taper between the main body and an upper portion of the splinting member;
   wherein the bottom portions of the first, second, third and fourth securing members have an adhesive material applied thereto;
   wherein a portion of the main body has an adhesive material applied thereto;
   wherein at least one of the main body, the securing members, and the splinting member comprise a flexible material configured to cover an active intravenous site and facilitate the flow of fluids into and out of the intravenous site;
   wherein an overall width of the intravenous splint cover is about 50% or less than an overall length of the intravenous splint cover;
   wherein a length of the main body is about 50% or less than the overall length of the intravenous splint cover;
   wherein a width of the main body is substantially equal to the overall width of the intravenous splint cover;
   wherein a length of the first, second, third and fourth securing member is about 25% or less than the overall length of the intravenous splint cover;
   wherein a width of each securing member is about 50% or less than the overall width of the intravenous splint cover;
   wherein a length of the splinting member is less than the length of the main body; and
   wherein a width of the splinting member is less than the width of the main body.

2. An intravenous splint cover according to claim 1 wherein the overall length of the intravenous splint cover is approximately 3.0 to 16.0 inches and the overall width of the intravenous splint cover is approximately 15% to 50% of the overall length of the intravenous splint cover.

3. An intravenous splint cover according to claim 1 wherein the overall length of the intravenous splint cover is approximately 6.0 to 18.0 inches.

4. An intravenous splint cover according to claim 1 wherein the overall length of the intravenous splint cover is about 10 inches and the overall width of the intravenous splint cover is about 2.75 inches.

5. An intravenous splint cover according to claim 1 wherein the length of the main body is approximately 0.5 to 6.0 inches and the width of the main body is approximately 15-50% of the overall length of the intravenous splint cover.

6. An intravenous splint cover according to claim 1 wherein the length of the main body is approximately 4.25 to 6.0 inches, 3.0 to 4.25 inches, or 1.0 to 3.0 inches.

7. An intravenous splint cover according to claim 1 wherein the width of the main body is approximately 3.0 to 6.0 inches, 2.75 to 5.0 inches, or 2.0 to 2.75 inches.

8. An intravenous splint cover according to claim 1 wherein the length of the main body is about 3.25 to 4.25 inches and the width of the main body is about 2.75 inches.

9. An intravenous splint cover according to claim 1 wherein the length of each of the pair of opposing securing members is approximately 5-25% of the overall length of the intravenous splint cover and the width of each of the pair of opposing securing members is approximately 15-50% of the overall width of the intravenous splint cover.

10. An intravenous splint cover according to claim 1 wherein the length of each of the pair of opposing securing members is about 2.875 inches and the width of each of the pair of opposing securing members is about 0.75 inches.

11. An intravenous splint cover according to claim 1 wherein the length of the splinting member is approximately 0.5 to 6.0 inches and the width of the splinting member is approximately 15-50% of the overall length of the intravenous splint cover.

12. An intravenous splint cover according to claim 1 wherein the length of the splinting member is about 1.5 to 2.0 inches and the width of the splinting member is about 2.25 to 2.75 inches.

13. An intravenous splint cover according to claim 1 wherein a thickness of the main body and the securing members is approximately 0.005 to 0.25 inches.

14. An intravenous splint cover according to claim 1 wherein a thickness of the splinting member is one of between about 0.005 and 0.125 inches and between about 0.0625 and 1.0 inches.

15. An intravenous splint cover according to claim 1 wherein the splinting member comprises a first and second splinting member; wherein the first splinting member is at least one of longer and wider than the second splinting member.

16. An intravenous splint cover according to claim 15 wherein the first splinting member is a foam pad; and wherein the second splinting member is a foam pad.

17. An intravenous splint cover according to claim 15 wherein the second splinting member is adhesively connected to the main body; and wherein the first splinting member overlies the second splinting member so that outer peripheral portions of the first splinting member are adhesively connected to the main body.

18. An intravenous splint cover according to claim 15 wherein a length of the first and second splinting member is approximately 1.0 to 2.5 inches and a width of the first and second splinting member is approximately 75-100% of the overall width of the intravenous splint cover.

19. An intravenous splint cover according to claim 15 wherein a length of the first splinting member is about 2.0 inches and a width of the first splinting member is about 2.75 inches; and wherein a length of the second splinting member is about 1.5 inches and a width of the second splinting member is about 2.25 inches.

20. An intravenous splint cover according to claim 15 wherein a thickness of the first and second splinting member is approximately 0.0625 to 1.0 inches.

21. An intravenous splint cover according to claim 1 wherein the main body and the pair of opposing securing members comprise at least one of a substantially flexible material, a biodegradable material, a hypoallergenic material, and a latex-free material.

22. An intravenous splint cover comprising:
   a main body that includes a bottom portion, a top portion, a first side and a second side;
   a first pair of securing members connected to and extending outwardly from the main body comprising:
      a first rectangular securing member, and
      a second rectangular securing member,
   a second pair of securing members extending outwardly from the second side of the main body and comprising:
      a third rectangular securing member, and
      a fourth rectangular securing member,
   a splinting member that is carried by the bottom portion of the main body comprising a longitudinal and latitudinal profile with a bell curved frustum extending upwardly from the main body to create an elevated portion of the main body, wherein the splinting member comprises a first and second splinting member and wherein the first splinting member is at least one of longer and wider than the second splinting member;
   wherein the splinting member comprises an undulated taper between the main body and an upper portion of the splinting member;
   wherein the bottom portions of the first, second, third and fourth securing members have an adhesive material applied thereto;
   wherein a portion of the main body has an adhesive material applied thereto;
   wherein at least one of the main body, the securing members, and the splinting member comprise a flexible material configured to cover an active intravenous site and facilitate the flow of fluids into and out of the intravenous site.

23. A method of using an intravenous splint cover that includes a main body that has a rectangular shape, the main body comprising a bottom portion, a top portion, a first side, and a second side; a first pair of securing members comprised of a first rectangular securing member and a second rectangular securing member that have a rectangular shape and connect to and extend parallel outwardly from the first side of the main body; and a second pair of securing members comprised of a third rectangular securing member and a fourth rectangular securing member that connect to and extend parallel outwardly from the second side of the main body, a splinting member comprising a longitudinal and latitudinal profile with a bell curved frustum shape and is carried by the bottom portion of the main body and extends upwardly from the main body with an undulated taper between the main body and an upper portion of the splinting member to create an elevated portion of the main body, and a pair of adhesive cover members, the method comprising:
   removing a portion of the pair of adhesive cover members so that an adhesive side of one set of opposing securing members and a portion of the main body are exposed;
   positioning the splinting member over an IV site;
   securing the one set of opposing securing members and the portion of the main body to skin of a patient;
   removing the opposing portion of the pair of adhesive cover members; and
   securing the opposing set of opposing securing members and the opposing portion of the main body to another portion of the skin of the patient or to the set of opposing securing members;
   wherein the bottom portions of the pair of opposing securing members have an adhesive material applied thereto;
   wherein a portion of the main body has an adhesive material applied thereto;
   wherein at least one of the main body, the securing members, and the splinting member comprise a flexible material configured to cover an active intravenous site and facilitate the flow of fluids into and out of the intravenous site;
   wherein an overall width of the intravenous splint cover is about 50% or less than an overall length of the intravenous splint cover;
   wherein a length of the main body is about 50% or less than the overall length of the intravenous splint cover;
   wherein a width of the main body is equal to the overall width of the intravenous splint cover;
   wherein a length of each securing member is about 25% or less than the overall length of the intravenous splint cover;
   wherein a width of each securing member is about 50% or less than the overall width of the intravenous splint cover;
   wherein a length of the splinting member is less than the length of the main body; and
   wherein a width of the splinting member is less than the width of the main body.

* * * * *